(12) United States Patent
Huang et al.

(10) Patent No.: US 9,877,978 B2
(45) Date of Patent: Jan. 30, 2018

(54) COMPOSITIONS COMPRISING NDGA DERIVATIVES AND SORAFENIB AND THEIR USE IN TREATMENT OF CANCER

(71) Applicant: THE JOHNS HOPKINS UNIVERSITY, Baltimore, MD (US)

(72) Inventors: Ru Chih Huang, Baltimore, MD (US); David Mold, Baltimore, MD (US); Christopher Ruland, Annapolis, MD (US); Yu-Chuan Liang, Baltimore, MD (US); Jong Ho Chun, Woodbine, MD (US)

(73) Assignee: The Johns Hopkins University, Baltimore, MD (US)

( * ) Notice: Subject to any disclaimer, the term of this patent is extended or adjusted under 35 U.S.C. 154(b) by 35 days.

(21) Appl. No.: 14/374,323

(22) PCT Filed: Feb. 4, 2013

(86) PCT No.: PCT/US2013/024595
§ 371 (c)(1),
(2) Date: Jul. 24, 2014

(87) PCT Pub. No.: WO2013/116821
PCT Pub. Date: Aug. 8, 2013

(65) Prior Publication Data
US 2015/0018302 A1 Jan. 15, 2015

Related U.S. Application Data

(60) Provisional application No. 61/594,743, filed on Feb. 3, 2012, provisional application No. 61/614,825, filed on Mar. 23, 2012.

(51) Int. Cl.
| | |
|---|---|
| *A61K 31/7016* | (2006.01) |
| *A61K 31/05* | (2006.01) |
| *A61K 31/44* | (2006.01) |
| *A61K 31/09* | (2006.01) |
| *A61K 45/06* | (2006.01) |

(52) U.S. Cl.
CPC .......... *A61K 31/7016* (2013.01); *A61K 31/05* (2013.01); *A61K 31/09* (2013.01); *A61K 31/44* (2013.01); *A61K 45/06* (2013.01)

(58) Field of Classification Search
None
See application file for complete search history.

(56) References Cited

U.S. PATENT DOCUMENTS

| | | |
|---|---|---|
| 6,291,524 B1 | 9/2001 | Huang et al. |
| 2009/0215835 A1 | 8/2009 | Wilhelm |
| 2010/0256232 A1 | 10/2010 | White et al. |
| 2012/0093932 A1* | 4/2012 | Li .................... A61K 9/0019 424/489 |

FOREIGN PATENT DOCUMENTS

WO WO2009/089366 A2 * 7/2009

OTHER PUBLICATIONS

Aragon-Ching, J. B. et al., BJU International, "Final analysis of a phase II trial using sorafenib for metastatic castration-resistant prostate cancer", 2008, vol. 103, pp. 1636-1640.*
Zavodovskaya, M., et al., "Nordihydroguaiaretic acid (NDGA), an inhibitor of the HER2 and IGF-1 receptor tyrosine kinases, blocks the growth of HER2-overexpressing human breast cancer cells", Journal of Cellular Biochemistry, (2008) vol. 103, pp. 624-635.
Lenihan, D., "Tyrosine kinase inhibitors: can promising new therapy associated with cardiac toxicity strengthen the concept of teamwork?", Journal of Clinical Oncology, (2008) vol. 26, No. 32, pp. 5154-5155.

* cited by examiner

*Primary Examiner* — Layla D Berry
*Assistant Examiner* — Bahar Craigo
(74) *Attorney, Agent, or Firm* — John Hopkins Technology Transfer

(57) ABSTRACT

The present invention provides pharmaceutical compositions comprising derivatives of NDGA, including M4N (tetra-O-methyl nordihydroguaiaretic acid) and sorafenib and their use in the inhibition and treatment of neoplastic diseases, such as liver cancer, colon cancer, breast cancer, brain cancers and ovarian cancers, for example, in a subject. Compositions comprising derivatives of NDGA, including M4N, sorafenib and additional therapeutic agents are also provided.

11 Claims, 17 Drawing Sheets

Effect of combination treatment with $M_4N$ and sorafenib on liver histology in human hepatocellular carcinoma xenograft tumor-bearing nude mice

FIGURE 11

| Drugs | Parameters[a] | | | CI[b] value at | | | | DRI[c] value at | | | |
|---|---|---|---|---|---|---|---|---|---|---|---|
| | $D_m$ | m | r | $ED_{50}$ | $ED_{75}$ | $ED_{90}$ | $ED_{95}$ | $ED_{50}$ | $ED_{75}$ | $ED_{90}$ | $ED_{95}$ |
| M4N | 290.49 | 0.46 | 0.68 | | | | | 290.49 | 3158.66 | 34346.20 | 174086.00 |
| Sor | 29.10 | 4.05 | 0.96 | | | | | 29.10 | 38.16 | 50.05 | 60.18 |
| M4N + Sor | 49.66 | 3.49 | 0.90 | 0.68 | 0.61 | 0.62 | 0.64 | | | | |

FIGURE 12

| Drugs | Parameters[a] | | | CI[b] value at | | | | DRI[c] value at | | | |
|---|---|---|---|---|---|---|---|---|---|---|---|
| | $D_m$ | m | r | $ED_{50}$ | $ED_{75}$ | $ED_{90}$ | $ED_{95}$ | $ED_{50}$ | $ED_{75}$ | $ED_{90}$ | $ED_{95}$ |
| M4N | 79.44 | 3.55 | 0.95 | | | | | 3.73 | 3.94 | 4.17 | 4.33 |
| Sor | 111.30 | 3.55 | 0.89 | | | | | 5.23 | 5.52 | 5.84 | 6.06 |
| M4N + Sor | 42.59 | 4.32 | 0.87 | 0.46 | 0.43 | 0.41 | 0.40 | | | | |

COMPOSITIONS COMPRISING NDGA DERIVATIVES AND SORAFENIB AND THEIR USE IN TREATMENT OF CANCER

CROSS-REFERENCE TO RELATED APPLICATIONS

This application is a 35 U.S.C. § 371 U.S. national entry of International Application PCT/US2013/024595 having an international filing date of Feb. 4, 2013, which claims the benefit of U.S. Provisional Patent Application Nos. 61/594,743, filed on Feb. 3, 2012, and 61/614,825, filed on Mar. 23, 2012, the content of each of the aforementioned applications is herein incorporated by reference in their entirety.

BACKGROUND OF THE INVENTION

Carcinogenesis is a multistage event affected by a variety of genetic and epigenetic factors and is typified by the outbreak of uncontrolled cell growth originated from different tissues. A universal goal for anticancer research lies in the development of a clinical treatment that is highly effective in curtailment of tumor growth, non-toxic to the host, and is affordable for most patients. Drugs that inhibit targets that are unique to dividing cells, particularly cells dividing in an uncontrolled manner, are an ideal paradigm for chemotherapeutic agents, the greater the specificity to cells that are dividing in an uncontrolled manner the lower the risk of attendant side effects.

The inventors and colleagues have previously reported that tetra-O-methyl nordihydroguaiaretic acid ($M_4N$), also known as EM 1421 and terameprocol, a semi-chemically synthesized derivative of nordihydroguaiaretic acid (NDGA) possessed antiviral and anti-cancer activities in cultured cells, in mouse models, and in human xenografts in nude mice. As a transcription inhibitor, $M_4N$ suppresses Sp1-regulated cdk expression and causes cell cycle arrest at the G2 phase of the cell cycle.

Sorafenib inhibits the enzyme RAF kinase, a critical component of the RAF/MEK/ERK signaling pathway that controls cell division and proliferation. In addition, it blocks tumor angiogenesis via inhibition of tyrosine kinases in the VEGFR-2/PDGFR-beta signaling cascade. It is currently approved for the treatment of hepatocellular carcinoma (HCC) and renal cell carcinoma (RCC) and is under investigation for use in non-responsive thyroid cancer and glioblastoma. M4N (tetra-O-methyl nordihydroguaiaretic acid) is an Sp1 transcription inhibitor developed in our laboratory that has been shown to act synergistically with the kinase inhibitors UCN-01, rottlerin and LY294002 in the induction of rapid death in human prostate cancer cells.

As such, there still exists a need for novel and synergistic therapies for the treatment of neoplastic diseases.

SUMMARY OF THE INVENTION

In accordance with an embodiment, the present invention provides a pharmaceutical composition comprising an effective amount of nordihydroguaiaretic acid (NDGA) or a derivative thereof of formula I:

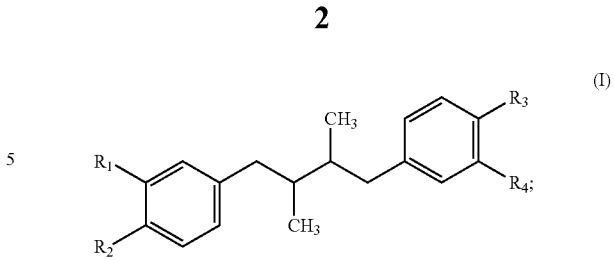

wherein $R_1$, $R_2$, $R_3$ and $R_4$ independently represent hydroxy, a straight or branched chain lower alkyl or alkoxy, an amino acid residue, a substituted amino acid residue, a nitrogen-containing 5- or 6-membered heterocyclic ring or a saccharide residue; the amino acid residue, substituted amino acid residue, nitrogen-containing 5 or 6 membered heterocyclic ring or saccharide residue being optionally joined to the phenyl ring by a linker of an oxygen atom and 1-10 carbon atoms; and an effective amount of sorafenib.

In accordance with another embodiment, the present invention provides a pharmaceutical composition comprising an effective amount of tetra-o-methyl nordihydroguaiaretic acid (M4N) or maltose-M3N, and an effective amount of sorafenib.

In accordance with an embodiment, the present invention provides a pharmaceutical composition comprising an effective amount of formula (II):

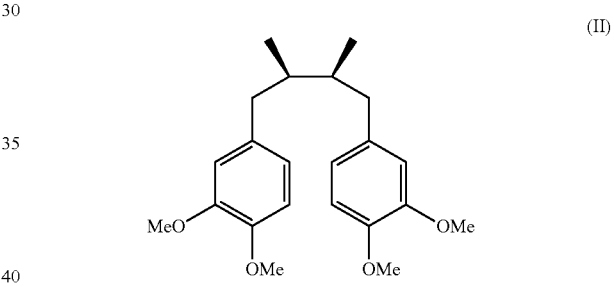

or a salt, solvate, or stereoisomer thereof, and an effective amount of sorafenib.

In accordance with a further embodiment, the present invention provides a use of the pharmaceutical compositions described above, an amount effective for use in a medicament, and most preferably for use as a medicament for treating a disease or disorder associated with a neoplastic disease in a subject.

In accordance with yet another embodiment, the present invention provides a use of the pharmaceutical compositions described above, and at least one additional therapeutic agent, in an amount effective for use in a medicament, and most preferably for use as a medicament for treating a disease or disorder associated with a neoplastic disease in a subject.

BRIEF DESCRIPTION OF THE DRAWINGS

FIG. 11. Dose-effect relationships of M4N, alone and in combination with sorafenib, in AsPc-01 human pancreatic carcinoma cells after 48 h treatment. [a]Dm, median effect dose (concentration in micromoles/liter that inhibits cell growth by 50%). m, shape of the dose-effect curve (m=1, hyperbolic; m>1, sigmoidal; m<1, negative sigmoidal). R, linear correlation coefficient of the median effect plot. [b]CI, combination index, (CI<1, synergism; CI=1, additive effect; CI>1, antagonism): For mutually nonexclusive drugs, CI= (D1/Dx1)+(D2/Dx2)+(D1D2)/(Dx1Dx2). Dx1 and Dx2 are the doses of drug 1 (M4N) and drug 2 (Sorafenib) which are required to affect a given system by x % (x=50, 75, 90, 95). [c]DRI, dose reduction index (measured by comparing the doses required to reach a given degree of inhibition when using the drug as single agent and in combination)

FIG. 12. Dose-effect relationships of M4N, alone and in combination with sorafenib, in MDA-MB468 human breast carcinoma cells after 24 h treatment. [a]Dm, median effect dose (concentration in micromoles/liter that inhibits cell growth by 50%). m, shape of the dose-effect curve (m=1, hyperbolic; m>1, sigmoidal; m<1, negative sigmoidal). R, linear correlation coefficient of the median effect plot. [b]CI, combination index, (CI<1, synergism; CI=1, additive effect; CI>1, antagonism): For mutually nonexclusive drugs, CI= (D1/Dx1)+(D2/Dx2)+(D1D2)/(Dx1Dx2). Dx1 and Dx2 are the doses of drug 1 (M4N) and drug 2 (Sorafenib) which are required to affect a given system by x % (x=50, 75, 90, 95). [c]DRI, dose reduction index (measured by comparing the doses required to reach a given degree of inhibition when using the drug as single agent and in combination).

DETAILED DESCRIPTION OF THE INVENTION

Figure 1:
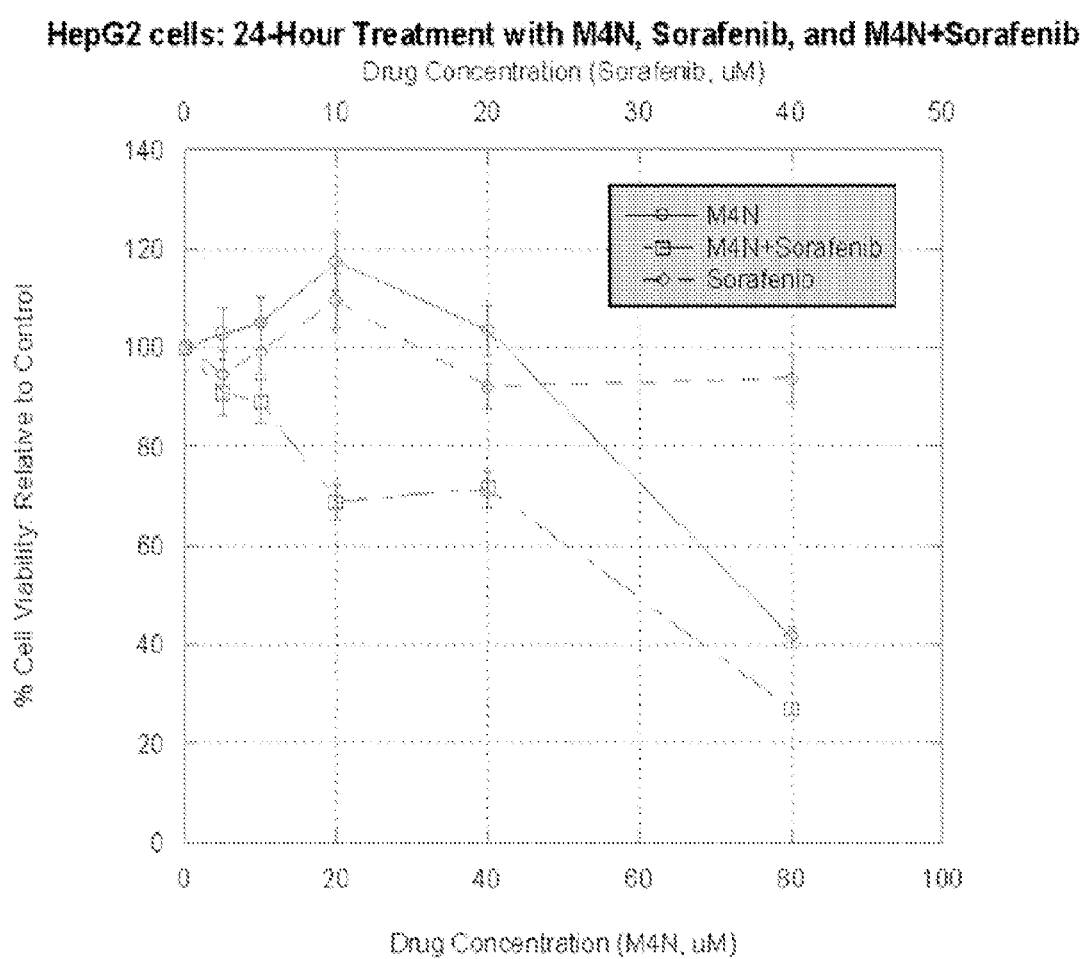
FIG. 1 depicts dose response curves for the cytotoxicity of M4N and sorafenib, alone and in combination in HepG2 cells after 24 h of treatment. The x-axis represents the dose of drug (μM) and the y-axis represent the percentage of viable cells relative to the untreated control.

In accordance with an embodiment, the present invention provides a pharmaceutical composition comprising an effective amount of nordihydroguaiaretic acid (NDGA) or a derivative thereof of formula I:

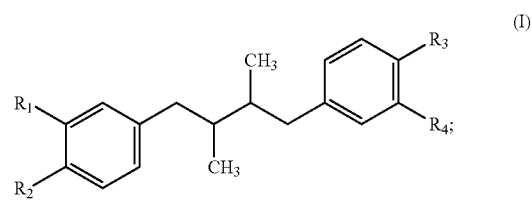

wherein $R_1$, $R_2$, $R_3$ and $R_4$ independently represent hydroxy, a straight or branched chain lower alkyl or alkoxy, an amino acid residue, a substituted amino acid residue, a nitrogen-containing 5- or 6-membered heterocyclic ring or a saccharide residue; the amino acid residue, substituted amino acid residue, nitrogen-containing 5 or 6 membered heterocyclic ring or saccharide residue being optionally joined to the phenyl ring by a linker of an oxygen atom and 1-10 carbon atoms; and an effective amount of sorafenib.

In another embodiment, the present invention provides pharmaceutical composition comprising a compound, salt, solvate, or stereoisomer of any of the above described compounds, at least one additional therapeutic agent, and a pharmaceutically acceptable carrier.

The chemical structure of sorafenib is:

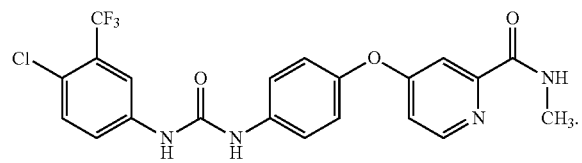 [SMILES: CNC(=O)c1cc(Oc2ccc(NC(=O)Nc3ccc(Cl)c(C(F)(F)F)c3)cc2)ccn1]

Included within the compounds of the present invention are the tautomeric forms of the disclosed compounds, isomeric forms including diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

With respect to the pharmaceutical compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include solid compositions such as solid-state carriers or latex beads.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

The choice of carrier will be determined, in part, by the particular pharmaceutical composition, as well as by the particular method used to administer the composition. Accordingly, there are a variety of suitable formulations of the pharmaceutical composition of the invention.

In accordance with an embodiment, the present invention provides a use of the pharmaceutical compositions disclosed herein in an amount effective for use in a medicament, and most preferably for use as a medicament for treating a disease or disorder associated with a neoplastic disease in a subject. In a preferred embodiment, the neoplastic disease is associated with a solid tumor, a hematological tumor, or wherein the tumor and/or its micro and macrometastases is selected from the group consisting of breast cancer, prostate cancer, pancreatic cancer, colon cancer, hepatoma, glioblastoma, ovarian cancer, leukemia, Hodgkin's lymphoma and multiple myeloma.

It will be understood to those of skill in the art that the term "therapeutic agent" is any agent capable of affecting the structure or function of the body of a subject or is an agent useful for the treatment or modulation of a disease or condition in a subject suffering therefrom. Examples of therapeutic agents can include any drugs known in the art for treatment of disease indications.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se, as well as pharmaceutically acceptable, pharmacologically active salts, esters, amides, prodrugs, metabolites, analogs etc.

In a further embodiment, the compositions and methods of the present invention can be used in combination with one or more additional therapeutically active agents which are known to be capable of treating conditions or diseases discussed above. For example, the compositions of the present invention could be used in combination with one or more known therapeutically active agents, to treat a proliferative disease such as a tumor or cancer. Non-limiting examples of other therapeutically active agents that can be readily combined in a pharmaceutical composition with the compositions and methods of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated. By way of example, and not intending to limit the invention, the dose of the pharmaceutical compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated.

As used herein, the terms "effective amount" or "sufficient amount" are equivalent phrases which refer to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease, such as a neoplastic disease or tumor Pharmaceutical compositions in accordance with the invention are useful for diagnosis, prognosis, prophylaxis or treatment of a condition. Accordingly, compositions in accordance with the invention are useful as a drug or as information for structural modification of existing compounds, e.g., by rational drug design. Compounds and methods of the invention are useful for screening compounds having an effect on a variety of conditions.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, intraperitoneally, intramuscular, or intradermal injections that provide continuous, sustained levels of the drug in the patient. Treatment of human patients or other animals are generally carried out using a therapeutically effective amount of a therapeutic of the invention in a physiologically-acceptable carrier. Suitable carriers and their formulation are described, for example, in Remington's Pharmaceutical Sciences by E. W. Martin.

The amount of the therapeutic agent to be administered varies depending upon the manner of administration, the age and body weight of the subject/patient, and with the subject's symptoms and condition. A compound is administered at a dosage that best achieves medical goals with the fewest corresponding side effects.

The pharmaceutical compositions of this invention including biologically active fragments, variants, or analogs thereof, can be administered by any suitable routes including intracranial, intracerebral, intraventricular, intrathecal, intraspinal, oral, topical, rectal, transdermal, subcutaneous, intravenous, intramuscular, intranasal, and the like. In one embodiment, the compositions are added to a retained physiological fluid, such as cerebrospinal fluid, blood, or synovial fluid. The compositions of the invention can be amenable to direct injection or infusion at a site of disease or injury.

As noted above, compositions of the invention can be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, cited herein.

For example, pharmaceutical compositions according to the invention may be in the form suitable for sterile injection. To prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate).

Suitable dosage forms can be formulated for, but are not limited to, oral, rectal, sublingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients. In a preferred embodiment, the dosage form is suitable for injection or intravenous administration.

To prepare such pharmaceutical dosage forms, one or more of the aforementioned compounds are intimately admixed with a pharmaceutical carrier according to conventional pharmaceutical compounding techniques. The carrier may take a wide variety of forms depending on the form of preparation desired for administration.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

Compositions for parenteral use may be provided in unit dosage forms (e.g., in single-dose ampules), or in vials containing several doses and in which a suitable preservative may be added. The composition may be in the form of a solution, a suspension, an emulsion, an infusion device, or a delivery device for implantation, or it may be presented as a dry powder to be reconstituted with water or another suitable vehicle before use. The composition may include suitable parenterally acceptable carriers and/or excipients.

In one approach, a therapeutic of the invention is provided within an implant, such as an osmotic pump, or in a graft comprising appropriately transformed cells. Methods of introduction may also be provided by rechargeable or biodegradable devices. Various slow release polymeric devices have been developed and tested for the controlled delivery of drugs, including proteinacious biopharmaceuticals. A variety of biocompatible polymers (including hydrogels), including both biodegradable and non-degradable polymers, can be used to form an implant for the sustained release of a bioactive factor at a particular target site.

Generally, the amount of administered agent of the invention (dosage) will be empirically determined in accordance with information and protocols known in the art.

Compositions of the invention can comprise various pharmaceutically acceptable salts, ether derivatives, ester derivatives, acid derivatives, and aqueous solubility altering derivatives of the active compound. The present invention can comprise all individual enantiomers, diastereomers, racemates, and other isomer of compounds of the invention. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benzenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention.

Prodrugs and active metabolites of compounds of the invention are also within the scope of the invention.

A prodrug is a pharmacologically inactive compound that is converted into a pharmacologically active agent by a metabolic transformation. In vivo, a prodrug is acted on by naturally occurring enzyme(s) resulting in liberation of the pharmacologically active agent. Conventional procedures for the selection and preparation of suitable prodrug derivatives are described, for example, in "Design of Prodrugs", ed. H. Bundgaard, Elsevier, 1985.

An active metabolite is a compound which results from metabolism of another compound after administration of the latter to a subject. Metabolites can be identified by techniques well-known in the art.

It is also contemplated that in an embodiment of the present invention, the methods of treatment disclosed herein are useful against many mammalian tumors, including, for example, breast cancer, prostate cancer, pancreatic cancer, colon cancer, hepatoma, glioblastoma, ovarian cancer, leukemia, Hodgkin's lymphoma and multiple myeloma.

It will be understood by those of ordinary skill in the art that the term "tumor" as used herein means a neoplastic growth which may, or may not be malignant. Additionally, the compositions and methods provided herein are not only useful in the treatment of tumors, but in their micrometastses and their macrometastses. Typically, micrometastasis is a form of metastasis (the spread of a cancer from its original location to other sites in the body) in which the newly formed tumors are identified only by histologic examination; micrometastases are detectable by neither physical exam nor imaging techniques. In contrast, macrometastses are usually large secondary tumors.

In accordance with an embodiment, the present invention provides compositions and methods for the prevention and/or treatment of tumors, and their micrometastses and their macrometastses.

EXAMPLES

Cytotoxicity assay. HepG2 human HCC cells were seeded at a density of $5 \times 10^4$ cells per well in 24 well plates and 24 h later the growth medium was supplemented with M4N, sorafenib, or a combination of the two drugs. M4N was used at concentrations between 0 and 80 µM. For the combination of M4N and sorafenib a constant molar ratio of 2:1 (M4N:sorafenib) was used. Twenty four hours after drug addition, cytotoxicity was assessed with the MTT assay with 540 measured with a Power Wave 200 microplate reader. Cytotoxicity was also measured for cells treated with increasing concentrations of sorafenib (0-160 µM) with, and without a constant concentration of M4N (60 µM).

Evaluation of drug interactions. The combination index (CI) isobologram method of Chou and Talalay, which is based on the median-effect principle, was used to calculate synergism or antagonism for the combined drug effects. Dose-effect curves for the two drugs, singly and in combination, in serially diluted concentrations were plotted using the median-effect equation and plot and the CI equation and plot. CI values at different effect and dose levels and isobolograms were generated automatically using the computer software CompuSyn. With this method, additive, synergistic, or antagonistic effects are indicated by CI values of 1, <1, and >1, respectively. Comparison of the ratio of doses required to reach a given effect level for each single drug and the drugs in combination was used to determine the dose-reduction.

Animals. T cell-deficient nude (nu/nu) mice, males and females 5 to 6 weeks of age, were purchased from Charles River Laboratories. The nude mice were housed in a pathogen-free room and all experiments involving the mice were carried out in accordance with the Johns Hopkins University Animal Care and Use Committee guidelines.

Tumor models. T cell-deficient nude (nu/nu) mice were implanted s.c. in their flanks with cultured human tumor cells suspended in HBSS/Matrigel (50:50, v/v). When the tumors exhibited a mean diameter of 4-8 mm, the mice were assigned to a treatment group that received M4N, sorafenib or a combination of the two drugs and a control group that received the vehicle only. To ensure that the M4N-treated groups and the control groups started with approximately equal distributions of tumor sizes, the mice were grouped into one of three categories: those bearing small tumors (<4 mm in length), medium tumors (4-8 mm), and large tumors (>8 mm) Both control and M4N-treated groups received roughly equal numbers of mice from each of the three categories.

Figure 15:
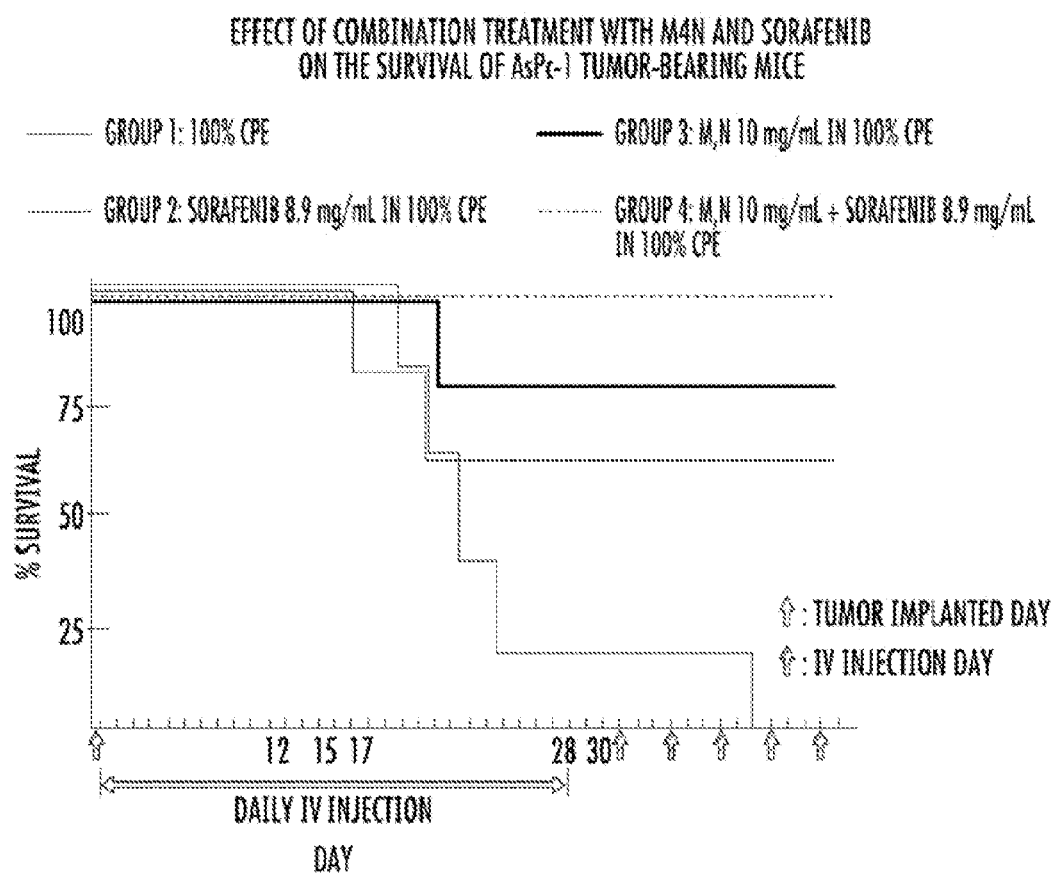
FIG. 15. Cumulative survival rates of AsPc-1 tumor-bearing mice evaluated according to treatment groups.
Figure 16:
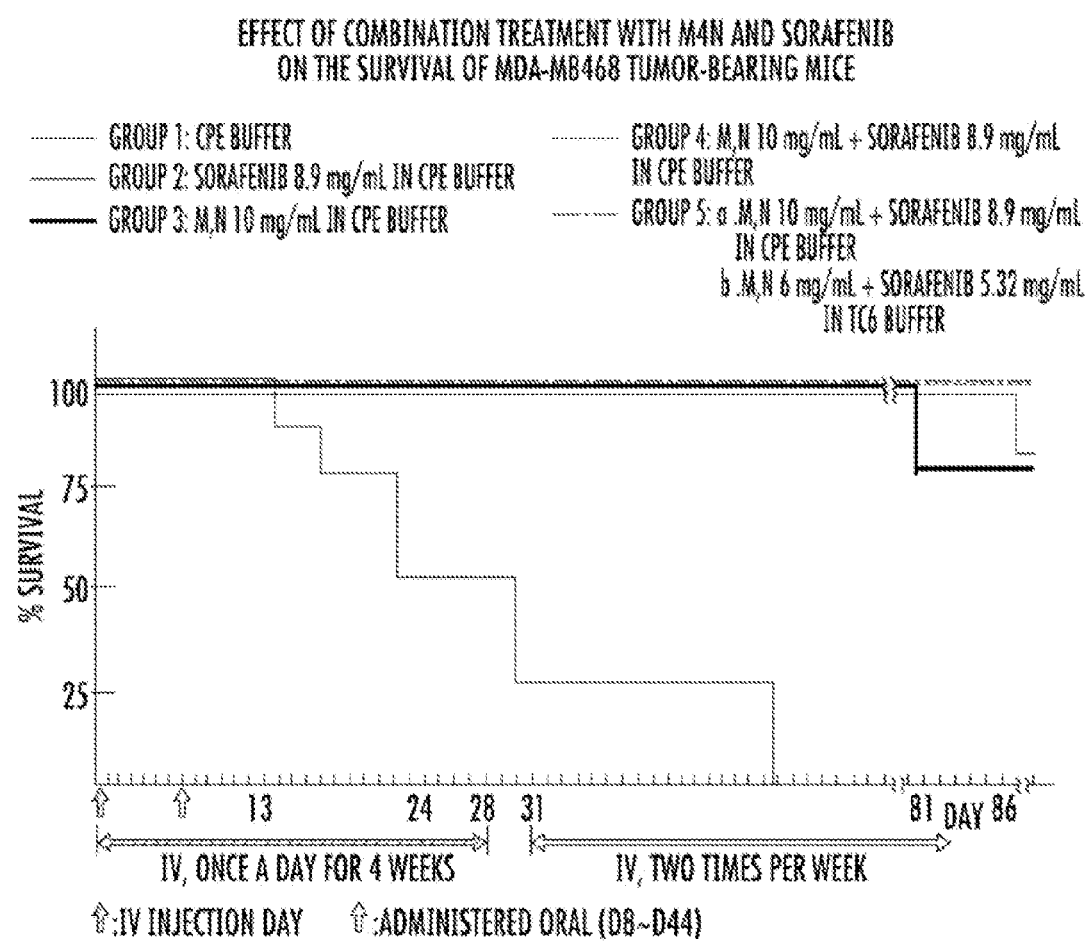
FIG. 16. Cumulative survival rates of MDA-MB468 tumor-bearing mice evaluated according to treatment groups.

Administration of M4N to tumor-explanted nude mice. For i.v. and oral administration, M4N and sorafenib were dissolved in the cyclodextrin-based CPE solvent system (Erimos Pharmaceuticals) Mice received a single daily i.v. tail vein injection or were force fed by oral gavage with an animal feeding needle according to the dosing schedules outlined in FIGS. 6, 15 and 16.

Evaluation of antitumor effect. Tumors were measured in two perpendicular dimensions once every 7 days, and the tumor volumes were calculated according to the formula: $V=(a^2 \times b)/2$, where a is the width of the tumor (smaller diameter) and b is the length (larger diameter). The relative tumor volume (RTV) of each tumor was defined as the ratio of the volume at a given time and the volume at the start of treatment (5). The mean RTV and SE was calculated for each treatment group. At the termination of the experiment, the tumors were excised and fixed in formaldehyde. Tissue samples were then sectioned and mounted for histological staining with hematoxylin and eosin.

Western immunoblot analysis. Treated and control cells were washed with PBS and suspended in RIPA buffer (150 mM NaCl, 50 mM Tris-HCL (pH8.0), 0.1% SDS, 1% NP40, and 0.5% deoxycholate) supplemented with protease inhibitor cocktail. After a 20 min incubation on ice, the suspension was centrifuged to clear the solubilized proteins. Bradford protein assay were performed and samples containing equivalent amounts of protein were resolved by standard SDS-polyacrylamide gel electrophoresis and transferred to nirocellulose membrane. The membranes were blocked with skim milk, and incubated with primary antibodies at 4° C. overnight and then with secondary antibody conjugated with horse radish peroxidase at room temperature for 1 h. The signals were detected by western blot chemiluminescence detection reagent.

Example 1

Evaluation of the combined effect of M4N and sorafenib. M4N and sorafenib, in combination, inhibited the growth of the HCC human cancer cell line HepG2 in a dose-dependent manner (FIG. 1). The cytotoxic activity of the drug combination was dramatically enhanced when compared to the activity of either drug alone.

Figure 2:
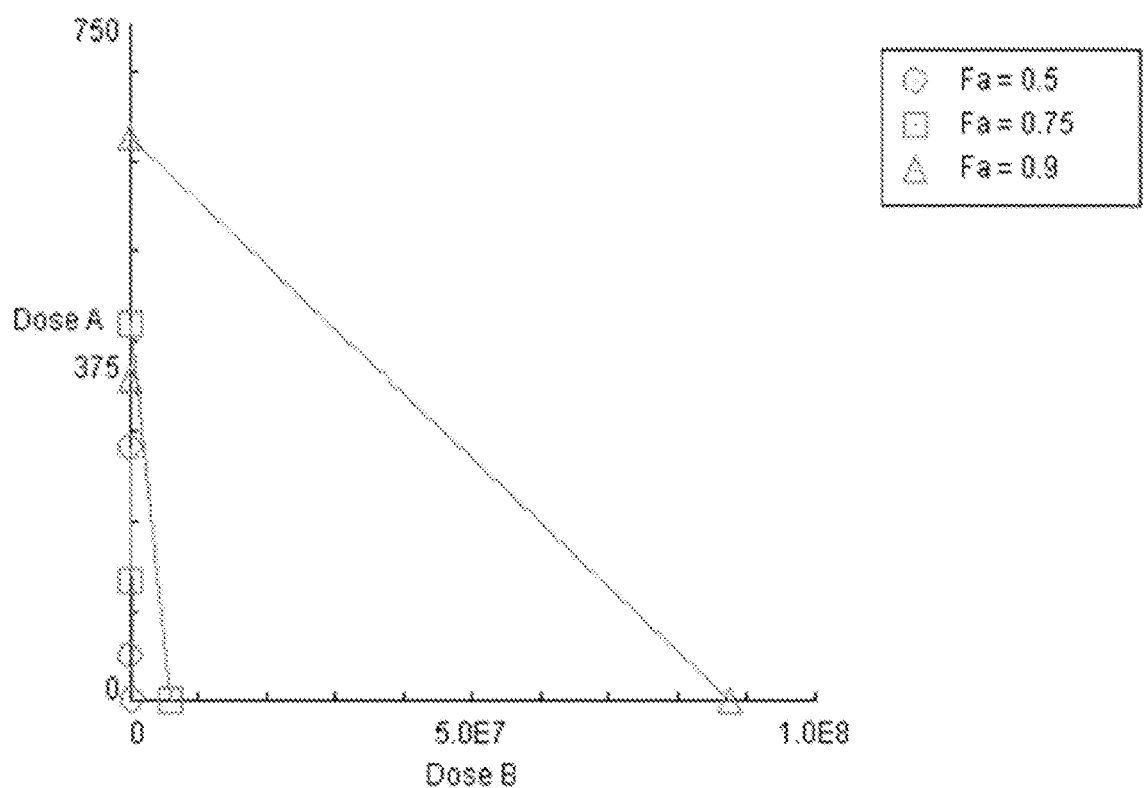
FIG. 2 shows isobologram analysis of the combination of M4N with sorafenib in HepG2 cells at different effect levels (Fa). Combination data points located on the hypotenuse, lower left, and upper right, represent additive effect, synergism, and antagonism, respectively.

Two methods, the isobologram method and the CI method, were used to determine if there is synergy between sorafenib. Isobolograms were constructed for the doses of M4N and sorafenib necessary to inhibit growth 90% (Fa=0.9), 75% (Fa=0.75), and 50% (Fa=0.5). The experimental data points for the M4N and sorafenib drug combination in HepG2 cells were at drug concentrations below the expected additive effect line for each of these values, indicating that there is a synergy between M4N and sorafenib (FIG. 2).

Figure 3:
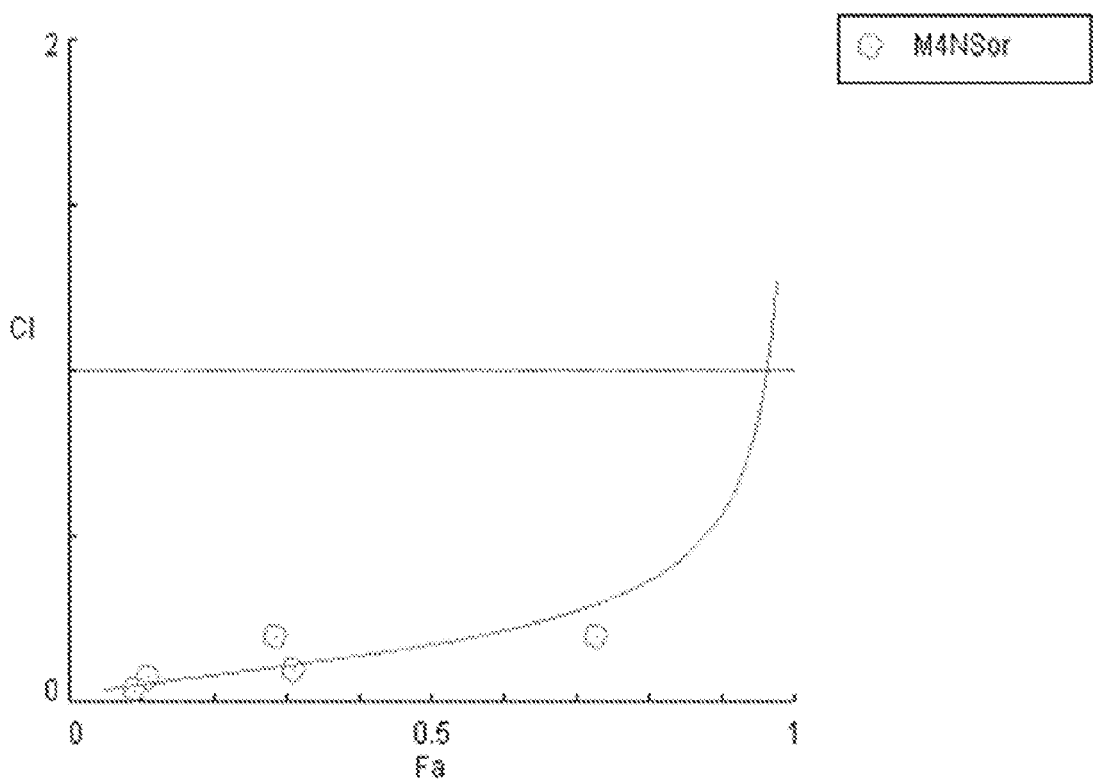
FIG. 3 shows CI plot analysis of the combination of M4N with sorafenib in HepG2 cells. CI=1, <1, and >1 indicates additive effect, synergism, and antagonism, respectively.

The median effect analysis of Chou and Talalay was used to calculate the combination index (CI) for the drug combination of M4N and Sorafenib. The combination was strongly synergistic (CI<0.3) at ED50, synergistic (CI<0.7) at ED75 and ED90, and moderately synergistic (CI<0.85) at ED95 (Table 1 and FIG. 3).

Figure 4:
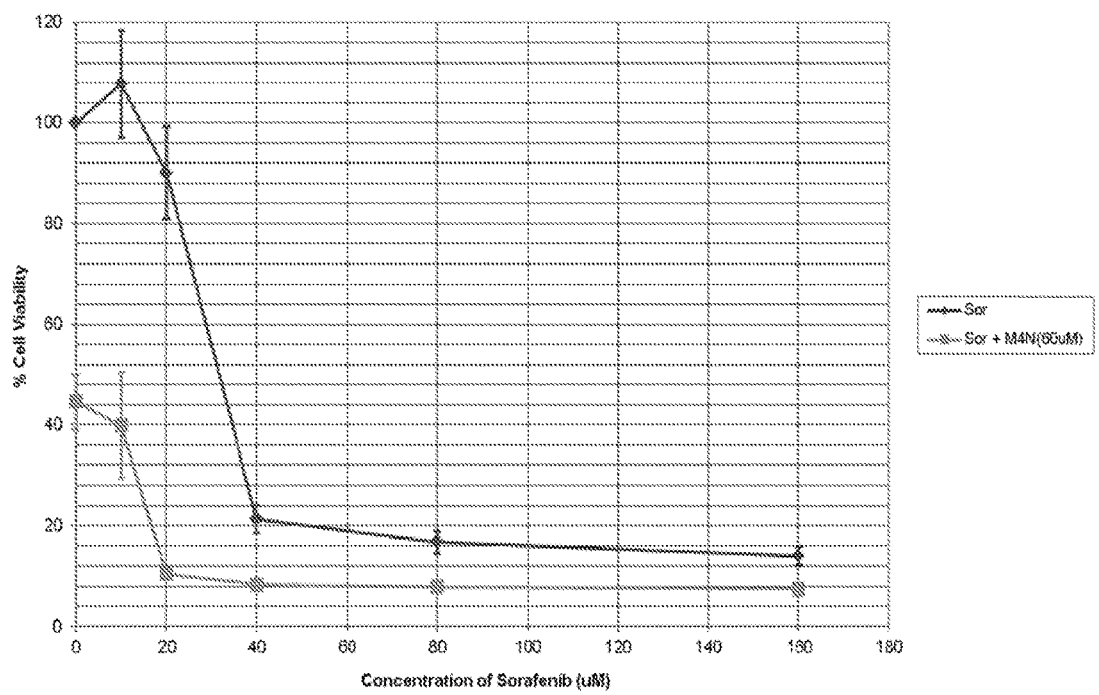
FIG. 4 depicts dose response curves for the cytotoxicity of sorafenib, alone and in combination with 60 μM M4N in HepG2 cells after 24 h of treatment. The x-axis represents the dose of Sorafenib (μM) and the y-axis represents the percentage of viable cells relative to the untreated control.

Dose response curves were also generated for cells treated with increasing concentrations of sorafenib alone or in combination with 60 μM M4N. These results (FIG. 4) showed that the $IC_{50}$ of sorafenib against HepG2 cells after 24 h of treatment is approximately 30 μM. The data also showed that while the cytotoxic effect of sorafenib at a concentration of 20 μM was only ~20%, when combined with 60 μM M4N it was nearly 90% effective (FIG. 4).

Example 3

Figure 5:
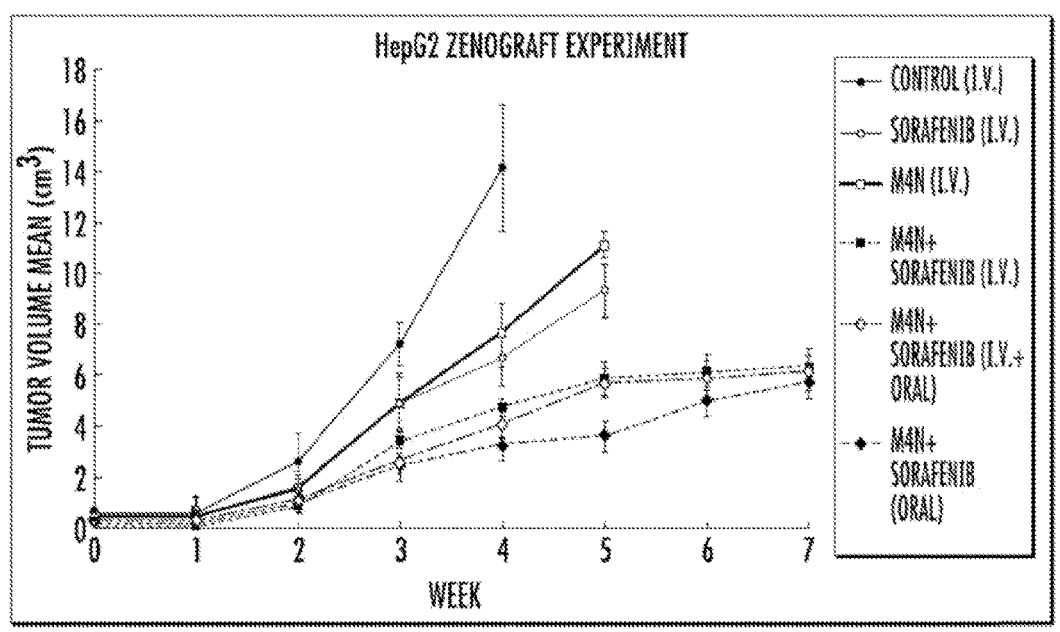
FIG. 5. Effect of combination treatment with M4N and sorafenib on the growth of HepG2 human hepatocellular carcinoma xenografts in nude mice.
Figure 6:
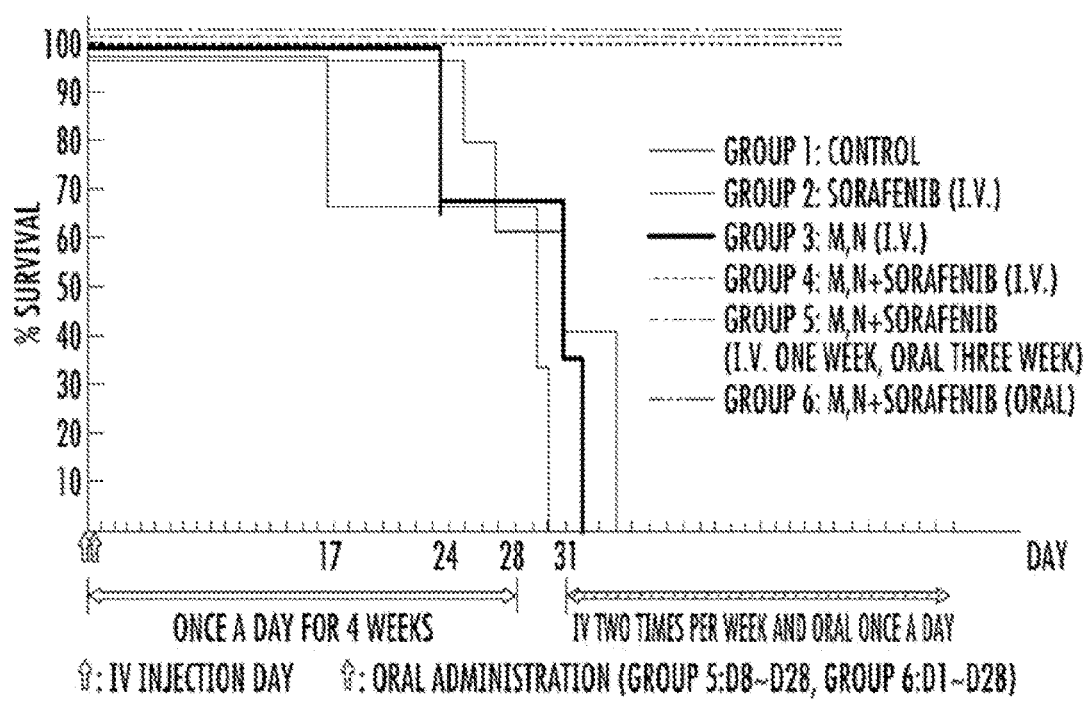
FIG. 6. Cumulative survival rates of HepG2 tumor-bearing mice evaluated according to treatment groups.
Figure 7:
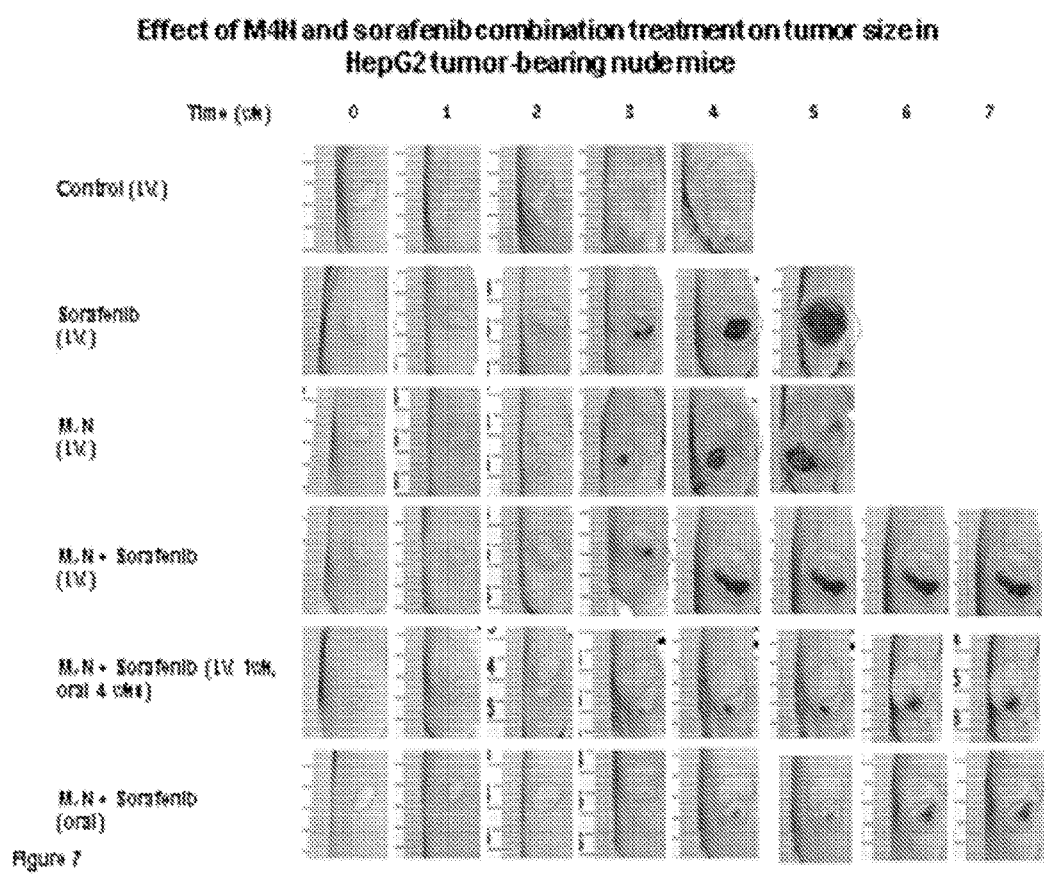
FIG. 7. Photographic documentation of the effect of M4N and sorafenib combination treatment on tumor size in HepG2 tumor-bearing nude mice.

Effect of combination treatment on human hepatocellular carcinoma tumor explants in nude mice: Human hepatocellular carcinoma xenograft tumors were established in nude mice for preclinical testing of the effectiveness of the M4N and sorafenib drug combination. Three groups of mice treated with various regimens of M4N combined with sorafenib were compared with mice treated with each drug alone or with only the CPE vehicle. After 5 weeks of treatment the results showed that for the two parameters tested, tumor growth and survival, the combination of M4N and sorafenib was much more effective when compared to the control and single drug groups (FIGS. 5, 6). Regardless of the route of administration, either i.v., oral, or a combination of the two; after 4 weeks of treatment, tumor growth was arrested in the combination treatment groups compared to the other groups (FIG. 5) and mouse survival was dramatically increased (FIG. 6). Results further showed that after 3 additional weeks of maintenance therapy consisting of twice weekly i.v. administration and daily oral dosing, there was 100% survival of the mice treated with the M4N and sorafenib combination, while none of the single treatment or control group mice remained alive (FIG. 6). The mouse deaths were due to increased tumor burden as demonstrated by photographs showing the presence of large tumors in the control and single drug treated groups (FIG. 7).

TABLE 1

Dose-effect relationships of M4N, alone and in combination with sorafenib, in HepG2 (hepatocellular carcinoma) cells: 24-Hour Treatment

| Drugs | Parameters[a] | | | CI[b] value at | | | | DRI[c] value at | | | |
|---|---|---|---|---|---|---|---|---|---|---|---|
| | $D_m$ | m | r | $ED_{50}$ | $ED_{75}$ | $ED_{90}$ | $ED_{95}$ | $ED_{50}$ | $ED_{75}$ | $ED_{90}$ | $ED_{95}$ |
| M4N | 282.53 | 2.76 | 0.71 | | | | | 5.67 | 3.15 | 1.75 | 1.17 |
| Sr | 438098 | 0.41 | 0.16 | | | | | 17583.1 | 92815.6 | 489945.0 | 1519041 |
| M4N/Sr | 74.75 | 1.11 | 0.93 | 0.18 | 0.32 | 0.57 | 0.85 | | | | |

[a]$D_m$, median effect dose (concentration in micromoles/liter that inhibits cell growth by 50%).
m, shape of the dose-effect curve (m = 1, hyperbolic; m > 1, sigmoidal; m < 1, negative sigmoidal).
R, linear correlation coefficient of the median effect plot.
[b]CI, combination index (CI < 1, synergism; CI = 1, additive effect; CI > 1, antagonism)
[c]DRI, dose reduction index (measured by comparing the doses required to reach a given degree of inhibition when using the drug as single agent and in combination)

Example 2

The dose reduction index (DRI) determines the fold dose-reduction allowed for each drug in synergistic combinations. This is important because dose reduction results in reduced toxicity while maintaining desired efficacy. As a result of their synergism, the DRI demonstrated a sizeable dose reduction for each of the drugs. The DRI indicated that the concentration of Sorafenib necessary to inhibit growth of 50%, 75%, 90%, and 95% of HepG2 cells (ED50, ED75, ED90, ED95) could be decreased 17,583.1, 92,815.6, 48,9945.0, and 151,9041 fold, respectively, by the concurrent administration of M4N (Table 1).

Example 4

Figure 8:
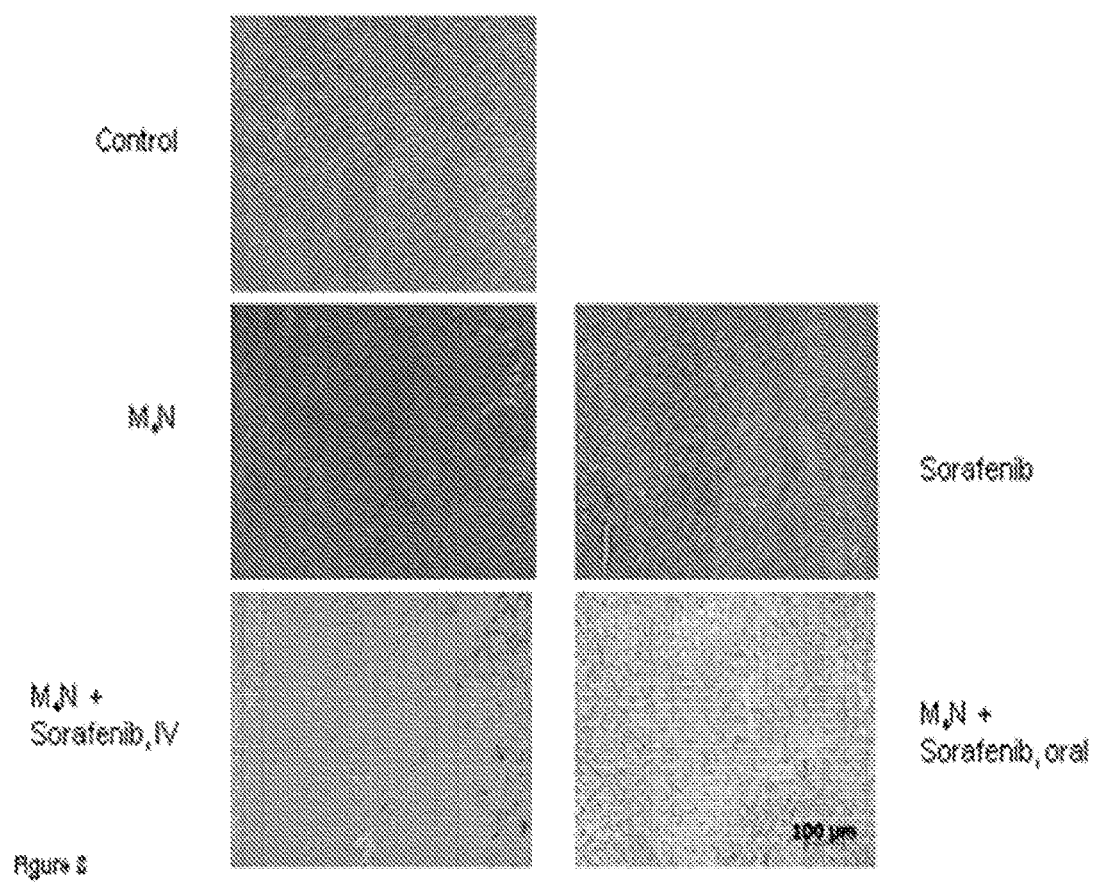
FIG. 8. Histological analysis of the effect of combination treatment with M4N and sorafenib on human hepatocellular carcinoma xenograft tumors with hematoxylin and eosin stained, formaldehyde fixed thin sections.
Figure 9:
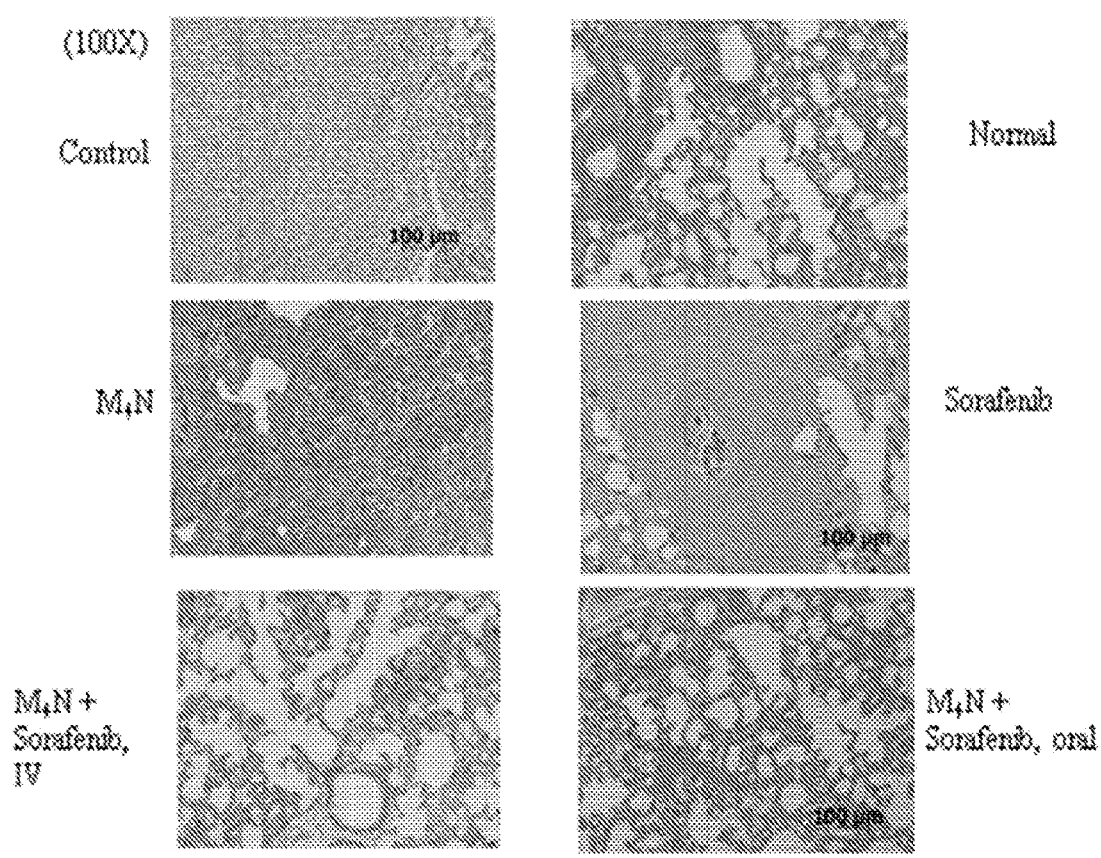
FIG. 9. Histological analysis of the effect of combination treatment with M4N and sorafenib on human hepatocellular carcinoma xenograft metastasis to the lung with hematoxylin and eosin stained, formaldehyde fixed thin sections.
Figure 10:
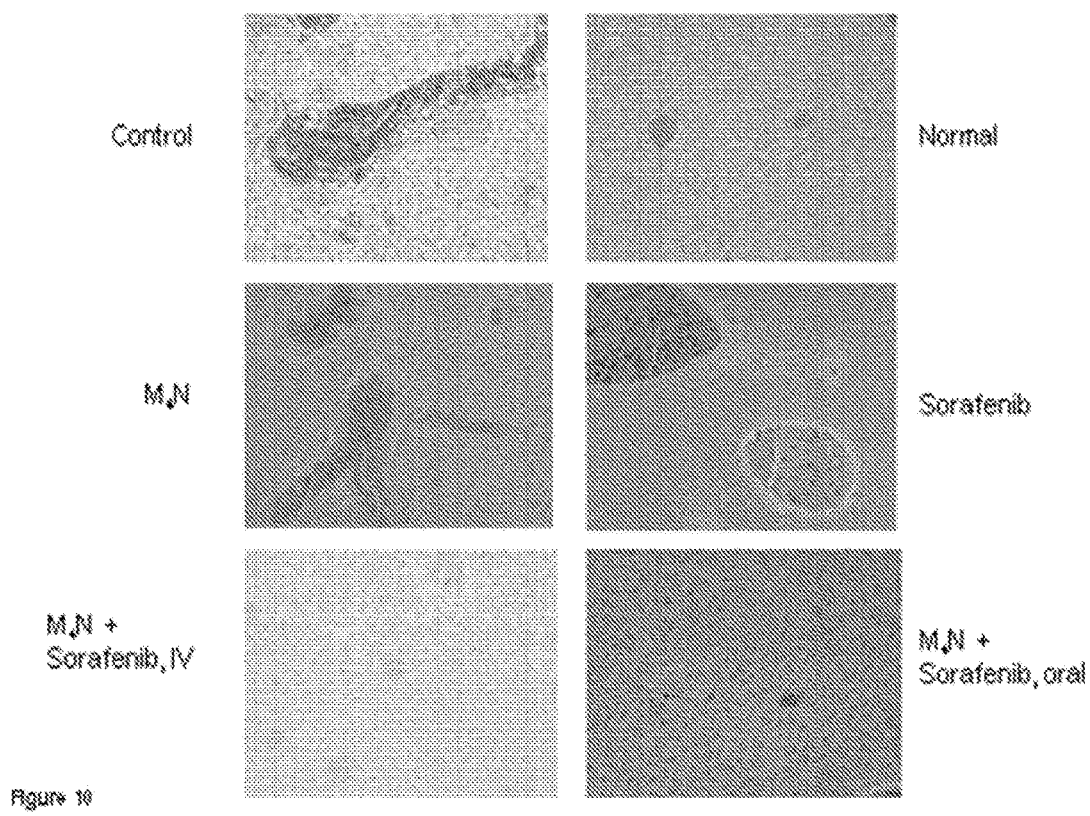
FIG. 10. Histological analysis of the effect of combination treatment with M4N and sorafenib on liver cytotoxicity in nude mice bearing human hepatocellular carcinoma xenograft tumors with hematoxylin and eosin stained, formaldehyde fixed thin sections.

Histological analysis of post mortem tissue biopsies of the mice was used to evaluate the cytotoxic effect of the drug combination on the tumor explants, the presence or absence of metastatic foci in the lungs and the effects, if any, on liver cytology. Examination of tumor tissue from each of the treatment groups revealed extensive loss of tumor cells in the combination treatment groups which was replaced by eosin-staining connective tissue fibrils (FIG. 8, lower panel). There was only mild tumor cell death visible in the tumor tissue from the single drug treated mice (FIG. 8, middle panel) and a robust population of tumor cells in the tumor tissue from the control mice. The lungs from mice in each group were examined grossly for the presence of tumor metastases. Metastases were present in the control and single drug treatment groups, but not in the group of mice treated with the drug combination. These results were confirmed by histological examination of lung tissue biopsies (FIG. 9), where the lungs of the drug combination mice were observed to be cytologically normal and free of micro metastases. Finally, no adverse effects of the combination drug treatment were observed in the mice. Further evidence of the safety of these drug regimens was established by histological examination of post mortem liver biopsies from the treated mice which showed no evidence of hepatotoxicity (FIG. 10).

Example 5

Effectiveness of combination treatment against other human cancers. Although cancers from different tissues and even those from the same tissue often have different molecular genetic origins, they all share the same general characteristics of unchecked growth control and overstimulated pro-survival pathways. Additional cell culture and animal studies were performed to determine if M4N, a global inhibitor of Sp1-dependent transcription and sorafenib, a multikinase inhibitor, are effective at treating a wider range of tumors from different tissue sources due to synergy between their respective growth arresting and apoptosis inducing properties. The drug combination was effective at killing cells in a synergistic manner from the following cancer cell lines: AsPc-1 (pancreas), MDA-MB468 (breast), HCT-116 (colon), FaDu (pharynx), OSC-19 (thyroid), LN229 (brain glioma), SKOV3 (ovarian), 786-0 (renal) and SW-780 (bladder). Combination index (CI) and dose reduction index (DRI) data are shown for two of the cell lines, pancreatic carcinoma AsPc-1 and breast carcinoma MDA-MB468 (FIGS. 11, 12) and these two cell lines were chosen for additional preclinical testing in explanted tumor-bearing nude mice.

Example 6

Figure 13:
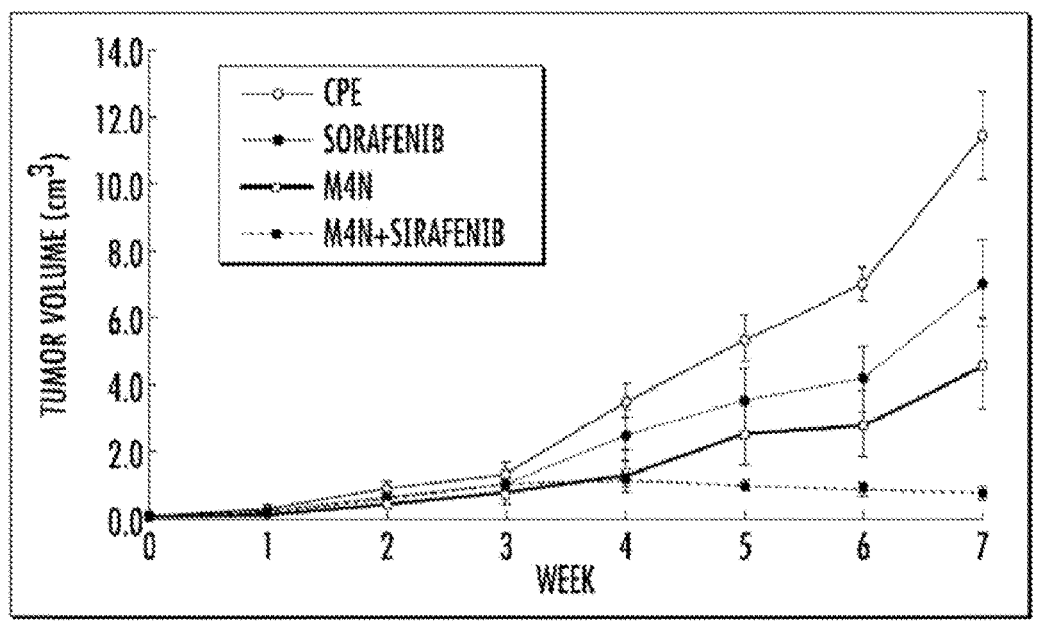
FIG. 13. Effect of combination treatment with M4N and sorafenib on the growth of AsPc-1 human pancreatic carcinoma xenografts in nude mice.
Figure 14:
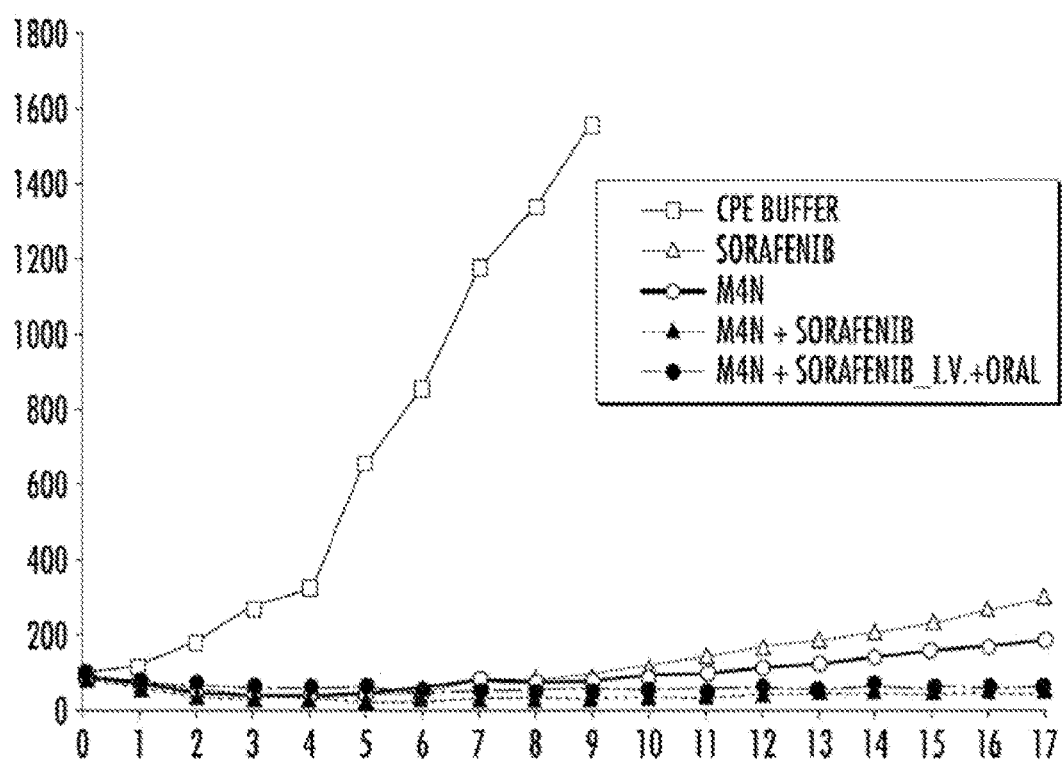
FIG. 14. Effect of combination treatment with M4N and sorafenib on the growth of MDA-MB468 human breast carcinoma xenografts in nude mice.

As was demonstrated for the human HepG2 hepatocellular carcinoma cells, both of the additional cell lines proved to be sensitive to treatment with the intravenous or orally administered M4N and sorafenib drug combination. Tumor growth (FIGS. 13, 14) was either arrested (MDA-MB468) or reversed (AsPc-1) and mouse survival rates (FIGS. 15, 16), although not 100%, were increased by the treatments. These data indicate that the drug combination is effective in a number of different cancers and may act in a more global manner than other more targeted therapies. Although the precise mechanism(s) of action of this combination of drugs has not completely been unraveled, the lack of toxicity demonstrated in these animal studies, suggests that these agents are active against pathways that are abnormally altered in a cancer-specific manner.

Example 7

Figure 17:
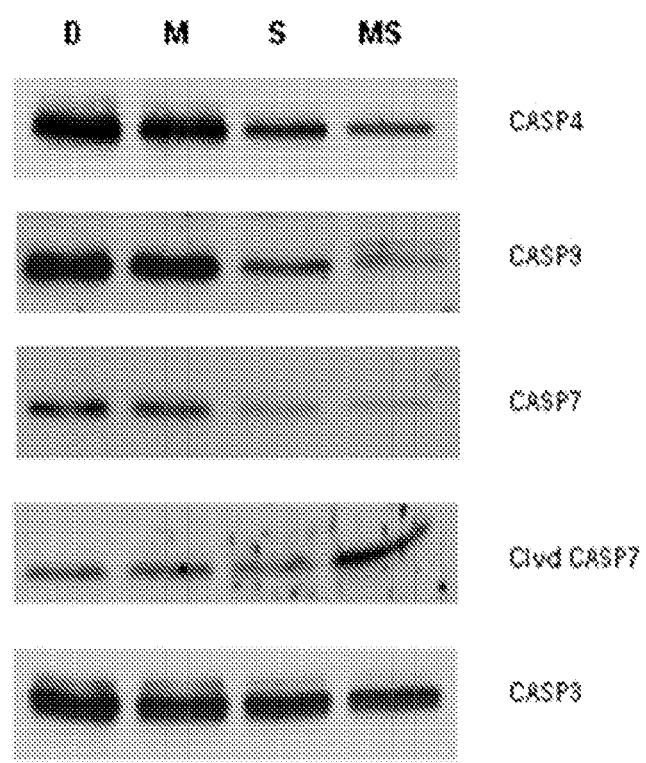
FIG. 17. Immunoblot analysis of caspase activation after treatment of AsPc-1 human pancreatic carcinoma cells with 1% DMSO vehicle (D), 80 μM M4N (M), 40 μM sorafenib (S) or a combination of 80 μM M4N and 40 μM sorafenib (M/S).

Mechanism of Action. The targeting of overexpressed pro-survival pathways has proved to be an effective anticancer strategy. Kinase inhibitors are often used to disrupt the protein kinase cascades involved in these pathways. M4N has been shown to inhibit Sp1-dependent transcription, thereby causing growth arrest and in some cases apoptosis through the inhibition of survivin expression. To determine if M4N acts to facilitate the apoptosis-inducing effects of sorafenib, proteins from cultured pancreatic cancer cells treated with M4N and sorafenib alone or in combination were analyzed by immunoblotting for caspase activation. The results (FIG. 17) show that sorafenib treatment alone resulted in decreased levels of procaspases 9, 4 and 7, suggesting caspase activation through procaspase cleavage. M4N had little effect on caspase activation when used alone, however when administered together with sorafenib, the two drugs greatly enhanced procaspase cleavage. More specific evidence for caspase 7 cleavage was observed using antibodies to detect the caspase 7 cleavage product (FIG. 17, panel 4) which was increased only after combination treatment. After 18 h of treatment, neither drug nor their combination had an effect on caspase 3 activation.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical composition comprising a synergistically effective amount of
   tetra-o-methyl nordihydroguaiaretic acid (M4N) or maltose-M3N; and
   a synergistically effective amount of sorafenib.

2. The pharmaceutical composition of claim 1, wherein the pharmaceutical composition comprises an additional therapeutic agent.

3. A method for treating a neoplastic disease in a subject comprising administering to the subject a synergistically effective amount of tetra-o-methyl nordihydroguaiaretic acid (M4N) or maltose-M3N; and a synergistically effective amount of sorafenib.

4. The method of claim 3 wherein the subject is a human.

5. The method of claim 3, wherein the neoplastic disease is a tumor and/or its micro and macrometastases.

6. The method of claim 5, wherein the tumor is selected from the group consisting of a solid tumor, a hematological tumor, or wherein the tumor and/or its micro and macrometastases is selected from the group consisting of breast cancer, prostate cancer, pancreatic cancer, colon cancer, hepatoma, glioblastoma, ovarian cancer, leukemia, and Hodgkin's lymphoma and multiple myeloma.

7. A method for treating or inhibiting a tumor and/or its micro and macrometastatic growth in a subject comprising administering to the subject a synergistically effective amount of tetra-o-methyl nordihydroguaiaretic acid (M4N) or maltose-M3N; and a synergistically effective amount of sorafenib.

8. The method of claim 7 wherein the subject is a human.

9. The method of claim 7, wherein the tumor is selected from the group consisting of a solid tumor, a hematological tumor, or wherein the tumor is selected from the group consisting of breast cancer, prostate cancer, pancreatic cancer, colon cancer, hepatoma, glioblastoma, ovarian cancer, leukemia, and Hodgkin's lymphoma and multiple myeloma.

10. The method of claim 7, wherein the pharmaceutical compositions comprises an additional therapeutic agent.

11. The method of claim 3, wherein the pharmaceutical composition comprises an additional therapeutic agent.

* * * * *